(12) United States Patent
Overman

(10) Patent No.: US 7,858,127 B2
(45) Date of Patent: *Dec. 28, 2010

(54) METHOD FOR ADMIXING PLANT ESSENTIAL OILS TO COATINGS FOR THE PURPOSE OF REPELLING INSECTS

(75) Inventor: Gregg R. Overman, Southaven, MS (US)

(73) Assignee: CTA Products Group, Inc., Southaven, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/393,825

(22) Filed: Feb. 26, 2009

(65) Prior Publication Data

US 2009/0155394 A1 Jun. 18, 2009

Related U.S. Application Data

(63) Continuation-in-part of application No. 11/411,084, filed on Apr. 25, 2006, now Pat. No. 7,514,102, which is a continuation-in-part of application No. 11/161,339, filed on Jul. 29, 2005, now abandoned.

(60) Provisional application No. 60/600,124, filed on Aug. 9, 2004.

(51) Int. Cl.
*A61K 36/00* (2006.01)
*A61K 36/752* (2006.01)

(52) U.S. Cl. ........................... 424/725; 424/736

(58) Field of Classification Search ................ None
See application file for complete search history.

(56) References Cited

U.S. PATENT DOCUMENTS

| 5,885,600 | A * | 3/1999 | Blum et al. ................. 424/405 |
| 6,881,248 | B2 * | 4/2005 | Lee et al. ................. 106/18.32 |
| 2005/0004233 | A1 * | 1/2005 | Bessette et al. ............. 514/730 |
| 2005/0063924 | A1 * | 3/2005 | Maniscalco .................. 424/59 |

* cited by examiner

*Primary Examiner*—Christopher R Tate
*Assistant Examiner*—Randall Winston
(74) *Attorney, Agent, or Firm*—Butler, Snow, O'Mara, Stevens & Cannada PLLC

(57) ABSTRACT

The Federal EPA has consistently limited the use of known toxicants (insecticides) to preclude their admixture into paints and coatings by contractors or homeowners for the purpose of repelling or killing insects on the dried or cured coating. The current invention is a method to repel, rather than kill, insects, arachnids, and other arthropods, utilizing materials taken from the EPA's GRAS (Generally Recognized as Safe) List, obviating onerous Federal Insecticide, Fungicide, and Rodenticide Act (FIFRA) regulations and greatly extending the useful life of the insect-repellant materials by binding them into the dried film solids—greatly slowing their evaporation and degradation and creating a timed release of insect repellant material. Furthermore, the current invention utilizes the insect repellant nature of these materials to repel insects from the surrounding area during coating application, thereby eliminating the need for applying insect repellants, such as DEET, to the skin.

30 Claims, No Drawings

METHOD FOR ADMIXING PLANT ESSENTIAL OILS TO COATINGS FOR THE PURPOSE OF REPELLING INSECTS

CROSS REFERENCE TO RELATED APPLICATIONS

This application is a continuation-in-part of U.S. application Ser. No. 11/411,084 filed Apr. 25, 2006, Ser. No. 11/161,339 filed Jul. 29, 2005, and No. 60/600,124, filed Aug. 9, 2004, hereby specifically incorporated by reference. Applicant Claims priority under 35 U.S.C. §120 and 119(e).

FIELD OF THE INVENTION

This invention relates to a method for admixing plant essential oils with coatings to provide insect repellant coatings.

BACKGROUND OF THE INVENTION

Various plant-derived essential oils have been used in numerous applications dating back to prehistory. Their use in repelling insects or animals is well-known. Because plant essential oils tend to be volatile and will evaporate quickly when exposed to the elements, they will not last long unless dissolved in a carrier such as mineral oil. Repelling insects from a surface for an extended period may be desirable so that spiders, wasps, Carpenter Bees, and many other undesirable insects will be deterred from crawling on, building nests on, or burrowing into the painted surface for an extended period.

There are products currently being marketed for admixture to paints for this purpose, but these materials are registered pesticides, functioning to kill rather than to repel insects, and are known to have significant toxicity in and of themselves. There are a limited number of products available today that use known insecticides to impart insecticidal properties to a dried paint film. In some applications, known insecticides may be added to a coating at the time of manufacture. Other products are sold with the intent that they be added to the liquid paint by the painter, contractor, or homeowner prior to painting. In this way, insecticidal qualities may be imparted to a paint, coating, or stain that previously did not exhibit such properties. DIAZINON (CIBA-GEIGY CORPORATION, Summit, N.J.) was registered for such a use and marketed under the name "CPF2D," (WALLA WALLA ENVIRONMENTAL, Inc., Walla Walla, Wash.), but it's registration for this use was discontinued. Numerous other materials have been used in this application, including DURSBAN (DOW AGRO SCIENCE, Indianapolis, Ind.) (Chlorpyrifos), but the Environmental Protection Agency (EPA) has consistently disallowed these applications presumably due to the inherent dangers of allowing consumers to admix known toxicants without training or instruction. Currently this inventor is aware of only one material being used for this purpose, i.e., a Deltamethrin product sold under the name "Bug Juice." It may well be that this labeled use will be disallowed in the near future. Another unintended consequence of mixing an insecticide with a paint or coating is that the dead insect may land in the freshly painted surface, ruining the finish.

There are also many products available today to repel insects from a given area or to deter insects, especially mosquitoes, from contacting the skin. The most well-known of these materials is N,N-diethyl-meta-toluamide or N,N-diethly-3-methylbenzamide (DEET). This is the active ingredient in such products as OFF (SC JOHNSON, Racine, Wash.) and many other commercially available insect repellants. It is well-known that many plants also produce compounds that are toxic or irritating to insects. Other plants may mimic the odor of these compounds to repel insects. There are many products made from plant oils being marketed today as insect repellants or insecticides.

Many plant essential oils and extracts thereof are known to be effective insect repellents and/or insecticides. The EPA, in the text of 40 CFR Part 152.25, refers to the materials found on its "Generally Regarded as Safe" (GRAS) List as "Minimum risk pesticides."

There are two previous patents outlining the use in coatings of various plant essential oils as deterrents to insect attack. U.S. Pat. No. 5,843,215 to Whalon et al. describes the use of essential oils for this purpose, but very narrowly defines this use to a maximum of 0.30% of essential oil added to clear, water-based print varnishes applied to flexible food packaging. On the other hand, it very broadly refers to "plant secondary compounds . . . which have insecticidal characteristics." It further describes the use of alcohols to aid in the dispersion of the essential oils and specifies the use of high speed equipment to accomplish same. This technique ensures that the utility of the previous patent will be limited to those who are versed in the art of manufacturing paints and coatings. U.S. Pat. No. 5,843,215 also differs from the current invention in that it does not describe nor does it teach the use of GRAS List materials to obviate onerous registration and expensive testing requirements. It does not describe or teach the simple stir-in practices of the current invention that enable anyone desiring an insect repellant coating to impart this property at a time and place of their choosing. U.S. Pat. No. 5,843,215 does not address the current invention wherein the desirous property of repelling noxious insects from an area during coating application is described.

U.S. Pat. No. 6,881,248 to Lee et al. addresses a much broader use of paint composition and thoroughly describes the longevity of insecticidal activity achieved by binding the insecticide into the coatings solids, as well as the advantages of dwellings with walls containing insecticide. However, U.S. Pat. No. 6,881,248 makes no mention of plant essential oils or of the GRAS List. Its major thrust is the use of piperonyl butoxide as a synergist to pyrethrums and the enhanced killing effect of this combination. This is a well-known synergy, and, apparently, this patent was awarded on the basis of describing this synergy in coating application. It differs from the current invention in that it does not describe, nor does it teach the use of GRAS List materials to repel rather than to kill insects. Neither does it describe or teach the Federal Insecticide, Fungicide, and Rodenticide Act (FIFRA) exempt status of GRAS List insecticides which allow any Do-It-Yourself applicator to impart insect repellency to a coating without undue regulatory restrictions and with minimal risk to themselves or the environment. It also differs from the current invention in that the desirous property of repelling noxious insects during coating application is described.

BRIEF SUMMARY OF THE INVENTION

The present invention provides a method whereby a homeowner, painter, contractor, or any other person who wishes, may impart a long-lived insect repellant property to a dried coating, paint, or stain which previously would not have had this characteristic. This method is applied to paints and coatings at the point of sale or at any time thereafter and advantageously utilizes naturally occurring plant essential oils or other materials taken from the EPA's GRAS list, thus removing the burden of onerous regulation and lessening the human health risks and environmental impact that might be encountered with conventional synthetic insecticides or repellents. The longevity of the insect repellant property is dependent upon the essential oils or mixtures thereof being encapsulated in the dried paint film or solids thereby greatly slowing their evaporation or degradation. More specifically, this invention provides a method whereby a homeowner, painter, contractor, or any other person who wishes may repel noxious insects such as mosquitoes and wasps from the immediate area during the application of the paint, stain, or other coating. The immediate area, under substantially wind-free conditions, is taken to be a buffer zone of some fifteen (15) feet from the area being painted. This characteristic of the invention removes the need for products, such as DEET, which must be applied directly to the skin. For the purposes of this invention, wind-free shall be taken to mean conditions in which the average or sustained wind velocity is one mile per hour or less.

DETAILED DESCRIPTION OF THE INVENTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The current invention describes the use of plant essential oils and plant extracts taken from the EPA's "Generally Recognized as Safe" GRAS list for the purpose of repelling or otherwise discouraging arthropods (insects and arachnids) from inhabiting, crawling upon, or burrowing into painted surfaces. This is accomplished by admixing the selected plant essential oil, or a mixture of these oils, into the bulk paint or coating prior to application. In this way, the oil or oils are incorporated into the dried paint film where it will remain for extended periods of time.

It is significant that the current invention describes a method whereby a user such as homeowners, contractors, and any Do-It-Yourselfer can impart an insect repellant nature to a paint which previously did not exhibit this property without undue regulatory difficulty and with what the EPA has determined is "insignificant risks to human health or the environment."

It is significant that the longevity of efficacy is dependent upon the plant essential oils being encapsulated in the film solids of the dried coating, paint, or stain. The current invention, in part, describes a method of extending the useful life of plant oils for the purposes of insect repellency via this encapsulation. The net effect is one of a timed release of the insect repellent materials, allowing the oils to be useful for months rather than days. Tests have shown that the insect repellant efficacy of such treated paints, coatings, and stains may, in some cases, last for twelve months or more.

It is significant that the current invention describes a method whereby a coating can be made to repel insects rather than kill them. Many products have been designed to kill insects on painted surfaces, however, no products have been designed that function by repelling insects. Repelling insects is advantageous because insects that die on a freshly painted surface ruin the finish and appearance.

It is also significant that the current invention describes a method whereby a painter, contractor, or homeowner may, at a time and place of their choosing, impart insect repellency to coatings which previously did not exhibit this property. Existing insecticides, such as the aforementioned DURSBAN (DOW AGRO SCIENCE, Indianapolis, Ind.) and Deltamethrin, may function quite well to stop insects from nesting on the cured paint, but they have no utility in repelling insects during the application of the coating.

Furthermore, the presence of the plant essential oils in the bulk liquid paint or stain has been shown to repel insects from the surrounding area during the application of the coating. This allows the painter to work efficiently without fear of being bitten or stung or having to apply a bug repellent.

Many plant oils and extracts are known to be effective as insecticides and/or insect repellants. The current invention describes a method of admixing one or more plant oils or extracts to a bulk liquid coating either at the point of sale of the coating or at some point thereafter, mixing the coating well, and then applying the coating as per the manufacturer's directions.

This coating may be variously referred to as paint, stain, wood oil, wood finish, wood seal, wood protectant, rust preventive coating, and any other liquid that is applied to a solid surface and later dries or cures. In general the coating will dry or cure via water loss in the case of latex coatings or via oxidative polymerization in the case of traditional alkyd (oil based) paints. However, there are any number of nontraditional coatings that could benefit from the current invention and that fall under our definition of coating. These might include lacquers, asphaltic materials, penetrating wood oils, wood preservatives, water repellants, and many others. The sole criteria for usefulness being that the coatings impart some solids to the substrate and thereby provide a material to retard the evaporation or degradation of the plant oil or plant extract.

The plant oils and extracts which are potentially useful in the current invention are numerous and varied. However, for the purposes of the current invention, we shall consider materials which the EPA has deemed to be of insignificant risk to human health and the environment and of known efficacy. Quoting from the EPA's statement during the promulgation of the ruling which generated the GRAS list: "EPA has determined, with the conditions imposed by this rule, that use of these pesticides poses insignificant risks to human health or the environment."

It is also beneficial, from the standpoint of regulatory complexity, to choose oils, extracts, and related compounds that are exempt from regulation by the Federal Insecticide Fungicide and Rodenticide Act (FIFRA). To quote once again from the EPA document that established the GRAS list: "This rule establishes an exemption from regulation under the Federal Insecticide, Fungicide, and Rodenticide Act (FIFRA) for certain pesticides. EPA has determined that these pesticides, under certain conditions, are of a character not necessary to be regulated under FIFRA in order to carry out the purposes of the Act. EPA has concluded that exemption of products covered by this final rule will not pose unreasonable risks to public health or the environment and will, at the same time, relieve producers of the burden associated with regulation."

A list of these materials can be found in 40 CFR Part 152.25. The current invention is not limited to those materials found on the GRAS List as of this date, but may include other materials when and if the EPA amends the GRAS List. As of the writing of this document, the components of the GRAS List that might be useful are as follows:

- Cedar oil
- Cinnamon and cinnamon oil
- Citric acid
- Citronella and Citronella oil
- Cloves and clove oil
- Eugenol
- Garlic and garlic oil
- Geraniol
- Geranium oil
- Lemongrass oil
- Linseed Oil
- Mint and mint oil
- Peppermint and peppermint oil
- Rosemary and rosemary oil
- Sesame (includes ground sesame plant) and sesame oil
- Thyme and thyme oil
- White pepper During practical application, a contractor, painter, homeowner, or any other person desiring to impart insect repellency to a paint, stain, or coating which previously lacked this property would add one or more of these oils or extracts to the coating at a rate of between 0.5 and 28 ounces of oil, extract, or mixture thereof, per gallon of paint, stain, or coating, not to exceed a total loading of 28 ounces per gallon and preferably at a rate of two to six ounces per gallon.

The addition of the plant essential oils would be accomplished either at the coating's point of sale or at some time between the sale of the coating and its application to the substrate.

The coating/essential oil or extract mixture would then be admixed together by paint shaker or thorough mixing with a spatula, mixer affixed to a drill, or some other implement or mechanical device until the coating is of a homogeneous appearance, and no visible striations or extraneous oily material are visible. The coating should then be applied as per the manufacturer's directions.

The resulting coating will contain the oil or extract and will repel and deter insects and arachnids of all types from nesting, crawling, or burrowing into the treated surface. The film solids of the coating will encapsulate and bind the essential oils, greatly increasing the useful life of these materials as insect repellants by imparting a timed release quality to the essential oils.

Plant essential oils applied topically and without a heavy mineral oil component will evaporate and become nonfunctional within a matter of hours or days. This varies greatly depending upon the particular essential oil and the ambient conditions. Higher heat and lower humidity tend to increase the rate of evaporation of these and other oils.

Plant essential oils encapsulated in the solid films of dried coatings have been shown to repel insects for twelve months and longer. This can vary greatly depending on exposure, the type of coating, coating thickness, the type and amount of essential oils present and many other factors including average annual temperature and rainfall in the area of the treated building, amount of sunlight striking the treated surface, environmental factors such as smoke and smog, salt water spray, etc.

The presence of the essential oil during application will deter wasps, mosquitoes and other noxious insects from inhabiting the surrounding area. Testing has shown a "buffer zone" of ten to fifteen feet around the area of coating application which insects such as mosquitoes and wasps will avoid. The depth of this buffer zone is highly dependent on wind conditions and will vary considerably depending on the type and amounts of essential oils present in the coating.

The establishment of this buffer zone during coatings application is extremely important to the comfort of the applicator. Use of the current invention obviates the need for personal insect repellants (such as DEET) which must be applied to the skin.

At the lower levels of addition, there are no expected adverse effects on the dried or cured paint film from the addition of the oil or extract.

Experimental Evidence

Experimental evidence using a "Preferred Box" type of testing has proven that insects will shun areas that have been painted with coatings containing Citronella, Cedar Wood Oil, Eugenol, Rosemary Oil and other materials from the GRAS List. The insects will preferentially inhabit the box painted with identical coatings but lacking the essential plant oil additives. In particular, a wooden box was constructed being 2.5 feet long, one foot wide, and one foot deep. The box is divided into three compartments by inserting pieces of one-quarter inch plywood properly cut to fit the box, with the middle compartment being six inches wide and the left and right compartments being one foot wide. A hole measuring three-fourths of an inch in diameter is drilled near the bottom and in the center of each of the two walls dividing the larger box. Two pine boards are cut to measure six inches by two inches. One of these boards is treated with a semi-transparent oil-based stain having a conventional alkyd resin binder. The other board is treated with the identical stain to which is added a blend of plant oils consisting of 85% Citronella, 5% Cedar Wood Extract, 5% Oil of Rosemary, 3% Eugenol, and 2% Lemongrass Extract. This blend is added at a rate of 3.2 ounces by volume (100 ml) to one gallon of ready-to-use stain. The boards are allowed to dry under ambient conditions of two days. At the end of that time, the board lacking the plant oils is placed in the right hand compartment of the box at the far right side, and the board with the plant oils is placed in the left hand compartment of the box at the far left side. Into the left and right portions of the box are placed identical food and water sources. In this case, apple slices and wet sponges were used. Crickets are purchased from a local bait shop, and thirty crickets are introduced to the middle compartment. A tight-fitting screen is applied to the top of the box. Note that there is no food source in the middle compartment and that the crickets can only obtain food by moving through the three quarter inch holes in the dividing walls and, therefore, into either the left or right hand compartments. Observations are made over a period of days, and it is found that the vast majority of the crickets are confined to the middle or right hand compartments. The left hand compartment (the one containing the board treated with the plant oils) is never found to contain more than two or three crickets.

Further embodiments of the claimed method include the use of any number of oils in the blend. We have successfully repelled insects from coated surfaces by admixing an insect repellent containing a single oil with the paint, stain, or wood finish. Using a blend of multiple oils in the admixture also worked well in repelling insects from a coated surface.

Embodiment Using Just One Oil.

A single oil may be used as the insect repellent to be admixed with the paint, stain, or wood finish. Any oil may be selected from the FIFRA exempt list that includes Cinnamon, Cedarwood, Geranium, Eugenol, Peppermint, Rosemary, Thyme, Citronella, and Lemongrass. The selected oil is effective in the range of 0.5 and 28 ounces per gallon of coating.

Rosemary oil's effectiveness was tested as an insect-repelling paint additive by admixing it with paint at the rate of three ounces per gallon. For the test, two equal aliquots of the same paint sample were apportioned, and one aliquot was admixed with Rosemary oil.

The two aliquots were then used to paint two identically-sized paint stir sticks (approximately 1 in.×9 in.×3/16 in.), and the paint was allowed to dry. Two coats were applied to each stick. One stick served as a "control" without any repellant, while the other stick served as the experimental subject and contained the repellent oil.

When dry, the two sticks were placed in a rectangular container (2 in.×10 in.×18 in.) with one stick at each end. Then, ten crickets were introduced into the container at the end with the treated stick, and the assembly was observed for 30 minutes. At intervals of one, three, five, ten, and thirty minutes, the number of crickets in each half of the container was counted, and photographs were taken at the 30 minute mark. The rating system was very conservative in that the crickets had to be repelled at least a considerable distance from the stick. The test results are shown below.

| Time Interval (Minutes) | Number of Crickets in Half with Treated Stick | Number of Crickets in Half with Untreated Stick |
| --- | --- | --- |
| 0 | 10 | 0 |
| 1 | 4 | 6 |
| 3 | 3 | 7 |
| 5 | 3 | 7 |
| 10 | 2 | 8 |
| 30 | 0 | 10 |

As can be seen from the table, after thirty minutes, no crickets remained on the side of the container that had the stick painted with a coating admixed with Rosemary oil. This indicates that Rosemary oil by itself is effective on its own as an additive to paints.

Embodiment Using Two Oils.

A blend consisting of two oils may be used effectively as the insect repellent to be admixed with the paint, stain, or wood finish. Any two oils may be selected from the FIFRA exempt list including Cinnamon, Cedarwood, Geranium, Eugenol, Peppermint, Rosemary, Thyme, Citronella, and Lemongrass. The selected oils are effective in the range of 0.5 and 28 ounces of combined volume per gallon of coating.

We tested the effectiveness of Rosemary oil and Citroneella oil as an insect-repelling paint additive by admixing both of them with paint at the rate of 3 oz of combined volume of oil per gallon. For the test, two equal aliquots of the same paint sample were apportioned, and one aliquot was admixed with Rosemary oil.

The two aliquots were then used to paint two identically-sized paint stir sticks, and the paint was allowed to dry. Two coats were applied to each stick. One stick served as a "control" without any repellant, while the other stick served as the experimental subject and contained the repellent oil.

When dry, the two sticks were placed in a rectangular container, as previously described, with one stick at each end. Then, ten crickets were introduced into the container at the end with the treated stick, and the assembly was observed for 30 minutes. At intervals of one, three, five, ten, and thirty minutes, the number of crickets in each half of the container was counted, and photographs were taken at the 30 minute mark. The test results are shown below.

| Time Interval (Minutes) | Number of Crickets in Half with Treated Stick | Number of Crickets in Half with Untreated Stick |
| --- | --- | --- |
| 0 | 10 | 0 |
| 1 | 4 | 6 |
| 3 | 3 | 7 |
| 5 | 3 | 7 |
| 10 | 4 | 6 |
| 30 | 2 | 8 |

As can be seen from the above chart, the combination of Rosemary oil and Citronella oil is successful in repelling insects. The vast majority of crickets moved to the side of the container that did not contain the stick which was coated with a paint containing the Rosemary and Citronella oils.

Embodiment Using Three Oils.

The above experiment was repeated using a different blend of oils. This blend contained Cinnamon, Geranium and Peppermint oils in equal parts. Once again, the efficacy of the oils as insect repellents when admixed with paint was tested as done above. The test results are shown below.

| Time Interval (Minutes) | Number of Crickets in Half with Treated Stick | Number of Crickets in Half with Untreated Stick |
| --- | --- | --- |
| 0 | 10 | 0 |
| 1 | 5 | 5 |
| 3 | 7 | 3 |
| 5 | 5 | 5 |
| 10 | 6 | 4 |
| 30 | 3 | 7 |

The results show that an insect repellent additive for paints, stains, and coatings could be made from Cinnamon, Gerarium, and Peppermint oils. Another combination of three oils was also tested.

Embodiment Using Three Oils (Second Blend).

The above experiment was repeated using a different blend of oils. This second blend contained Cinnamon, Thyme, and Citronella oils in equal parts. Once again, the efficacy of the oils as insect repellents when admixed with paint was tested as done above. The test results are shown below.

| Time Interval (Minutes) | Number of Crickets in Half with Treated Stick | Number of Crickets in Half with Untreated Stick |
| --- | --- | --- |
| 0 | 10 | 0 |
| 1 | 4 | 6 |
| 3 | 3 | 7 |
| 5 | 3 | 7 |
| 10 | 2 | 8 |
| 30 | 1 | 9 |

As can be seen from the results, different essential oils will have different effects.

Embodiment Using Four Oils.

A blend consisting of four oils may also be used effectively as the insect repellent to be admixed with the paint, stain, or wood finish. Any four oils may be selected from the FIFRA exempt list including Cinnamon, Cedarwood, Geranium, Eugenol, Peppermint, Rosemary, Thyme, Citronella, and Lemongrass. The selected oils are effective in the range of 0.5 and 28 ounces of combined volume per gallon of coating.

We tested the effectiveness of Cinnamon oil, Geranium oil, Citronella oil, and Rosemary oil as an insect-repelling paint additive by admixing the four oils in equal parts with paint at the rate of 5 ounces of combined volume of oil per gallon. For the test, two equal aliquots of the same paint sample were apportioned, and one aliquot was admixed with the selected oils.

The two aliquots were then used to paint two identically-sized paint stir sticks, and the paint was allowed to dry. Two coats were applied to each stick. Once again, one stick served as a "control" without any repellant, while the other stick served as the experimental subject and contained the repellent oil.

When dry, the two sticks were placed in a rectangular container, as previously described, with one stick at each end. Then, ten crickets were introduced into the container at the end with the treated stick, and the assembly was observed for 30 minutes. At intervals of one, three, five, ten, and thirty minutes, the number of crickets in each half of the container was counted, and photographs were taken at the 30 minute mark. The test results are shown below.

| Time Interval (Minutes) | Number of Crickets in Half with Treated Stick | Number of Crickets in Half with Untreated Stick |
|---|---|---|
| 0 | 10 | 0 |
| 1 | 6 | 4 |
| 3 | 4 | 6 |
| 5 | 3 | 7 |
| 10 | 3 | 7 |
| 30 | 2 | 8 |

As can be seen by the results, four oils are also effective in repelling insects from the painted surface.

Our previous experiments have shown that a blend of five oils works well in repelling insects. As verification of the methods of our previous tests, we performed the same experiment with five oils. Citronella, Cedar Wood Extract, Rosemary Oil, Eugenol, and Lemongrass extract were admixed such that the total oil rate was three ounces per gallon, and the admixture tested as above. In this case, one cricket was inadvertently injured and immobilized during insertion into the assembly so only nine crickets were counted. The results were:

| Time Interval (Minutes) | Number of Crickets in Half with Treated Stick | Number of Crickets in Half with Untreated Stick |
|---|---|---|
| 0 | 9 | 0 |
| 1 | 2 | 7 |
| 3 | 2 | 7 |
| 5 | 1 | 8 |
| 10 | 2 | 7 |
| 30 | 1 | 8 |

As seen by the above results, the painted surface containing the blend of five essential plant oils was very effective in repelling insects.

Results and Discussion.

In every case, shortly after introduction into the assembly, the crickets quickly began migrating away from the end with the repellant oil-containing stick. Within a few minutes, the predominant number of crickets was found away from the end with the repellant oil-containing stick. After 30 minutes, all, or nearly all, of the crickets were found away from the end with the repellant oil-containing stick. Note that the degree of repellency was based on the crickets being significantly away from the treated stick, i.e., over the half-way line. Thus, the repellency of the various oil admixtures was conclusively demonstrated.

The selection of the oils and the number of oils can be used to control the degree of repellency. In the two cases where blends of three oils were used, the second blend was clearly more effective than the first blend. Similarly, a single oil gave a similar performance as the blend of five oils. The oils to be used in a blend may also be chosen to create a particular pleasing fragrance or for greater efficacy as repellents.

Using the knowledge imparted herein, one skilled in the art could develop other blends that would act as repellants. However, this experimentation shows that the concept of incorporating one or more of the selected oils will effectively repel insects from coatings as claimed in the subject invention.

Tests have also been conducted in real-life situations, and it has been observed that Carpenter Bees will vacate previously infested structures when these structures are painted with coatings containing the essential oils. Further observation of treated and untreated areas has shown a lack of spider webs, wasp nests, Lady Bug infestations, and other signs of insect activity in the treated areas even when virtually-identical, untreated areas showed normal insect activity.

Observation of the absence of mosquitoes and wasps during the application of test materials led to the claim that coatings treated with these oils would repel these nuisance insects even as painting is in progress. This will be a boon to painters who have normally resorted to long-sleeved shirts and various preparations which must be applied to the skin, such as DEET.

Various mixtures of these oils and extracts may be found to be synergistic in their activity, or to have increased longevity, or to be more active against a particular pest when blended together. In this case, the invention might consist of blending the oils and extracts together and marketing the blend in this form for greater or more specific activity or longevity.

Having thus described the present invention, it is to be understood that the invention is not limited by particular details set forth in the above description, as many apparent variations are possible without departing from the spirit or scope thereof.

The invention claimed is:

1. A method comprising:
   a) admixing an insect repellant comprising rosemary oil with a coating to form an admixture; and
   b) applying a sufficient amount of said admixture to coat a surface and to provide insect repellant properties for twelve months or longer to said surface; wherein between 0.5 and 28 ounces of said insect repellant is added per gallon of the coating, and wherein the coating is selected from the group consisting of a paint, stain, wood oil, wood finish, wood seal, wood protectant, and rust preventive coating.

2. The method of claim 1 wherein the admixing occurs at the point-of-sale of said coating to said surface.

3. The method of claim 1 wherein the admixing occurs at the point-of-application to said surface.

4. The method of claim 1 wherein between two and six ounces of insect repellant is added per gallon of coating.

5. The method of claim 1 wherein the step of applying a sufficient amount of said admixture provides protection from insects to an applicator of said admixture.

6. A method comprising:
   a) admixing an insect repellant comprising a blend of citronella oil and rosemary oil with a coating to form an admixture; and
   b) applying a sufficient amount of said admixture to coat a surface and to provide insect repellant properties for twelve months or longer to said surface; wherein between 0.5 and 28 ounces of said insect repellant is added per gallon of the coating, and wherein the coating is selected from the group consisting of a paint, stain, wood oil, wood finish, wood seal, wood protectant, and rust preventive coating.

7. The method of claim 6 wherein the admixing occurs at the point-of-sale of said coating to said surface.

8. The method of claim 6 wherein the admixing occurs at the point-of-application to said surface.

9. The method of claim 6 wherein between two and six ounces of insect repellent is added per gallon of coating.

10. The method of claim 6 wherein the step of applying a sufficient amount of said admixture provides protection from insects to an applicator of said admixture.

11. A method comprising:
   a) admixing an insect repellant comprising a blend of cinnamon oil, geranium oil and peppermint oil with a coating to form an admixture; and
   b) applying a sufficient amount of said admixture to coat a surface and to provide insect repellant properties for twelve months or longer to said surface; wherein between 0.5 and 28 ounces of said insect repellant is added per gallon of the coating, and wherein the coating is selected from the group consisting of a paint, stain, wood oil, wood finish, wood seal, wood protectant, and rust preventive coating.

12. The method of claim 11 wherein the admixing occurs at the point-of-sale of said coating to said surface.

13. The method of claim 11 wherein the admixing occurs at the point-of-application to said surface.

14. The method of claim 11 wherein between two and six ounces of insect repellent is added per gallon of coating.

15. The method of claim 11 wherein the step of applying a sufficient amount of said admixture provides protection from insects to an applicator of said admixture.

16. A method comprising:
   a) admixing an insect repellant comprising a blend of cinnamon oil, thyme oil and citronella oil with a coating to form an admixture; and
   b) applying a sufficient amount of said admixture to coat a surface and to provide insect repellant properties for twelve months or longer to said surface; wherein between 0.5 and 28 ounces of said insect repellant is added per gallon of the coating, and wherein the coating is selected from the group consisting of a paint, stain, wood oil, wood finish, wood seal, wood protectant, and rust preventive coating.

17. The method of claim 16 wherein the admixing occurs at the point-of-sale of said coating to said surface.

18. The method of claim 16 wherein the admixing occurs at the point-of-application to said surface.

19. The method of claim 16 wherein between two and six ounces of insect repellent is added per gallon of coating.

20. The method of claim 16 wherein the step of applying a sufficient amount of said admixture provides protection from insects to an applicator of said admixture.

21. A method comprising:
   a) admixing an insect repellant comprising a blend of cinnamon oil, geranium oil, citronella oil and rosemary oil with a coating to form an admixture; and
   b) applying a sufficient amount of said admixture to coat a surface and to provide insect repellant properties for twelve months or longer to said surface; wherein between 0.5 and 28 ounces of said insect repellant is added per gallon of the coating, and wherein the coating is selected from the group consisting of a paint, stain, wood oil, wood finish, wood seal, wood protectant, and rust preventive coating.

22. The method of claim 21 wherein the admixing occurs at the point-of-sale of said coating to said surface.

23. The method of claim 21 wherein the admixing occurs at the point-of-application to said surface.

24. The method of claim 21 wherein between two and six ounces of insect repellent is added per gallon of coating.

25. The method of claim 21 wherein the step of applying a sufficient amount of said admixture provides protection from insects to an applicator of said admixture.

26. A method comprising:
   a) admixing an insect repellant comprising a blend of citronella oil, cedar oil, wood extract, rosemary oil, eugenol, and lemongrass extract with a coating to form an admixture; and
   b) applying a sufficient amount of said admixture to coat a surface and to provide insect repellant properties for twelve months or longer to said surface; wherein between 0.5 and 28 ounces of said insect repellant is added per gallon of the coating, and wherein the coating is selected from the group consisting of a paint, stain, wood oil, wood finish, wood seal, wood protectant, and rust preventive coating.

27. The method of claim 26 wherein the admixing occurs at the point-of-sale of said coating to said surface.

28. The method of claim 26 wherein the admixing occurs at the point-of-application to said surface.

29. The method of claim 26 wherein between two and six ounces of insect repellent is added per gallon of coating.

30. The method of claim 26 wherein the step of applying a sufficient amount of said admixture provides protection from insects to an applicator of said admixture.

\* \* \* \* \*